RASPBERRY PLANT

Filed Nov. 19, 1973

United States Patent

Plant Pat. 3,720

Patented May 20, 1975

3,720

RASPBERRY PLANT

John L. Franklin, Urbana, Ill., assignor to Herschel L. Boll, Champaign, Ill.

Filed Nov. 19, 1973, Ser. No. 417,430

Int. Cl. A01h *5/03*

U.S. Cl. Plt.—46 1 Claim

My invention relates to a new and distinct variety of raspberry plant. It was discovered by me as a chance seedling, a single plant growing under a tree in an uncultivated area of my lawn at Urbana, Ill., in 1968.

Since my discovery of the original plant, I have asexually reproduced a large number of plants from the original mother plant by tip layers.

My object in the asexual propagation of the original mother plant was to determine the characteristics of the plant and of its fruit by the testing of a large number of plants. The distinguishing features of my new variety have proved to be permanent. The plant has proved itself to have unusual possibilities because of its very vigorous growth, its very stocky canes, and its very large fruit.

Figure 2:
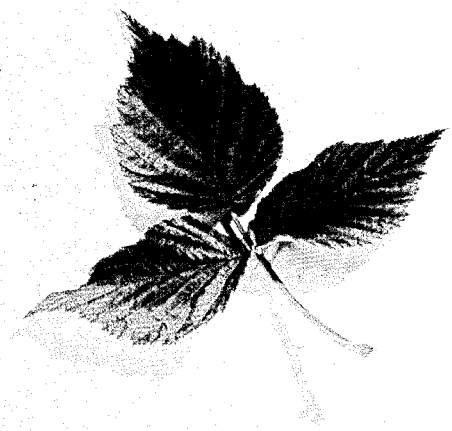
FIG. 2 is a typical leaf in full color.
Figure 1:
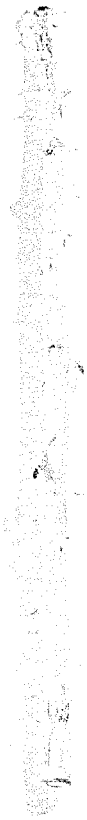
FIG. 1 shows a section of a typical primocane.
Figure 3:
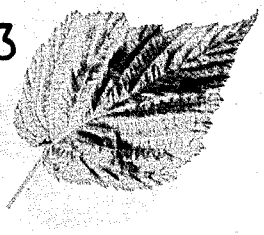
FIG. 3 shows a typical terminal leaflet.
Figure 4:
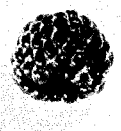
FIG. 4 illustrates a typical side view of a berry.
Figure 5:
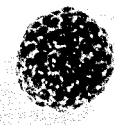
FIG. 5 shows a typical top view of a berry.

In general, the distinct and new variety of raspberry plant, which is the subject of my invention and discovery, is characterized by its very vigorous growth, by its very stocky canes, and by its very large fruit. These characteristics I now refer to in greater detail. Color plate references are according to Color Standards and Color Nomenclature by Robert Ridgway.

Under the conditions at Urbana, Ill., my new variety of plant is spring-bearing and high in productivity, producing under good culture, about 2½ to 4 quarts of fruit per plant, about the same amount as Ebonee (Plant Pat. No. 2,101) and Starking Blank Giant (Plant Pat. No. 1,494), slightly more than Black Hawk and Logan, and considerably more than Cumberland, Bristol, and Morrison. The plants are very vigorous, producing per year, up to 11 canes each and averaging about 8 to 10 canes. Logan, which my new variety probably most nearly resembles, averages about 7 to 8 canes, while Ebonee averages only 4 to 5 canes. The canes are very stocky, measuring up to ⅞ inch in diameter and averaging about ⅝ to ¾ inch, which is much more stocky than those of Logan and other varieties. The canes are erect and arching, reaching a height of about 4 to 5 feet. No suckers have been found on this new variety to date. The immature primocanes are medium green in color, sometimes reddish. The mature primocanes are dark purplish-red, or approximately Bordeaux (Plate XII), or varying from Pansy Purple (Plate XII) to Bordeaux (Plate XII) to Ox-blood Red (Plate I) after the bloom is rubbed slightly (except in some cases they are greenish on the unexposed surface), depending on exposure and soil, weather, and climatic conditions. The primocanes are glaucous, having much bloom. Prickles are medium green in color, sometimes reddish at the tips; are glaucous, and are medium in number and in size.

The leaves are medium green in color, or are approximately Forest Green (Plate XVII), or varying from Spinach Green (Plate V) to Forest Green (Plate XVII) to Cerro Green (Plate V), depending mainly on soil fertility, but also depending on other soil conditions, exposure and weather and climatic conditions. The leaves are medium in size. The terminal leaflets are cordate in shape. The lateral leaflets are oblanceolate with acuminate tip. The flowers are large. The date of the first blossoms in 1973 at Urbana, Ill., was May 20.

At Urbana, Ill., my new variety of raspberry plant begins to mature its fruit early and at about the same time as Logan. Cumberland, Bristol, and Starking Black Giant are midseason varieties, while Black Hawk, Morrison, and Ebonee are late. The date of the first picking in 1973 at Urbana, Ill., was June 17. The harvesting period is medium in length, or 10 to 14 days.

Under the conditions existng where I have reproduced and tested my new variety of raspberry plant, the fruit is very large, measuring up to ⅞ inch in diameter and averaging about ¾ inch, about the same size as Morrison, Starking Black Giant, and Ebonee, slightly larger than Black Hawk and Logan, and considerably larger than Cumberland and Bristol. The fruit is black in color, very pubescent between drupelets, hemispherical in shape, occasionally irregular at the base, relatively free from crumbling, firm, juicy, relatively sweet, and high in flavor. It is easily picked, separating readily from the receptacle. The number of berries per cluster is about 10 to 16, and the number of drupelets per berry ranges from about 60 to 90. The drupelets are medium in size.

My new variety of raspberry plant may not be especially resistant to any of the diseases; however, no virus diseases have been found on the plants of this variety to date. The raspberry above described, and the plant producing it, of course, may vary in slight details, depending on soil, weather, and climatic conditions.

What I claim is:

1. A new and distinct variety of raspberry plant substantially as herein shown and described characterized by its very vigorous growth, by its very stocky canes, and by its very large fruit.

References Cited

UNITED STATES PATENTS

P.P. 1,494 7/1956 Stouffer ---------- Plants—46

OTHER REFERENCES

Bountiful Ridge Nurseries, 1962–3 catalog, Princess Anne, Md., p. 42 relied on.

ROBERT E. BAGWILL, Primary Examiner